US00PP19979P3

(12) United States Plant Patent
Hambali

(10) Patent No.: US PP19,979 P3
(45) Date of Patent: May 12, 2009

(54) *AGLAONEMA* PLANT NAMED 'TWYAG0022'

(50) Latin Name: ***Aglaonema* hybrid**
Varietal Denomination: TWYAG0022

(75) Inventor: Gregori G. Hambali, Bogor (ID)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 22 days.

(21) Appl. No.: 11/903,760

(22) Filed: Sep. 25, 2007

(65) Prior Publication Data

US 2009/0083888 P1 Mar. 26, 2009

(51) Int. Cl.
*A01H 5/00* (2006.01)

(52) U.S. Cl. ..... Plt./376

(58) Field of Classification Search ..... Plt./376
See application file for complete search history.

*Primary Examiner*—Annette H Para
*Assistant Examiner*—Louanne C Krawczewicz Myers

(74) *Attorney, Agent, or Firm*—Jondle & Associates, P.C.

(57) ABSTRACT

A new *Aglaonema* plant particularly distinguished by having foliage that is medium to dark green and variably marked with spots and coalescing blotches of bright pink, primary veins that are pale green and flushed with pink, midribs that are pale green and variably tinged with pink, a dense, full, low spreading growth habit and intermediate in stature and yellow-green spathes, is disclosed.

1 Drawing Sheet

Genus and species: *Aglaonema* hybrid.
Variety denomination: 'TWYAG0022'.

BACKGROUND OF THE NEW PLANT

The present invention comprises a new and distinct cultivar of *Aglaonema,* botanically known as *Aglaonema* hybrid and hereinafter referred to by the variety name as 'TWYAG0022'. The new variety originated from an open pollination made in Bogor, West Java, Indonesia between unknown individual plants of *Aglaonema* (species unknown). The new variety was discovered as a single plant within the progeny of the stated open pollination in a controlled environment in Bogor, West Java, Indonesia.

The new variety was created in Bogor, West Java, Indonesia and has been asexually reproduced repeatedly by vegetative cuttings in Apopka, Fla. for two or more generations. The present invention has been found to retain its distinctive characteristics through successive asexual propagations.

SUMMARY OF THE INVENTION

The following are the most outstanding and distinguishing characteristics of the new variety when grown under normal horticultural practices in Apopka, Fla.

1. Foliage that is medium to dark green and variably marked with spots and coalescing blotches of bright pink;
2. Primary veins are pale green and flushed with pink;
3. Midrib is pale green and variably tinged with pink;
4. Dense, full, low spreading growth habit and intermediate in stature; and
5. Yellow-green spathes.

DESCRIPTION OF THE PHOTOGRAPH

This new *Aglaonema* plant is illustrated by the accompanying photograph which shows the overall plant habit and leaf color. The colors shown are as true as can be reasonably obtained by conventional photographic procedures.

DESCRIPTION OF THE NEW VARIETY

The following detailed description sets forth the distinctive characteristics of 'TWYAG0022'. The data which define these characteristics were collected from asexual reproductions carried out in Apopka, Fla. The plant history was taken on 12 month-old plants started from a single four-leaf rooted cutting, still in a vegetative state and grown in Apopka, Fla. Rooted cuttings were planted in 15 cm pots and grown in a greenhouse in August 2006. The plants were pinched once. Color readings were taken under natural light. Color references are primarily to the R.H.S. Colour Chart of the Royal Horticultural Society of London (R.H.S. (2001).

DETAILED BOTANICAL DESCRIPTION

Classification:
- *Family.*—*Araceae.*
- *Botanical.*—*Aglaonema* hybrid.
- *Common.*—Chinese Evergreen.
- *Cultivar name.*—'TWYAG0022'.

Growth:
- *Form.*—Low spreading and much wider than tall; new leaves emerge straight upright and mature leaves lean outward.
- *Growth and branching habit.*—Dense, full, low spreading growth habit and intermediate in stature.
- *Height* (*from soil to top of leaf plane*).—15 cm to 21 cm.
- *Diameter* (*area of spread, as measured from leaf tip to leaf tip across the canopy*).—42 cm to 57 cm.

*Growth rate.*—Somewhat slower than typical commercial *Aglaonema* varieties.

*Vigor.*—Plants produce axillary branches and numerous leaves; consistent progressive growth.

*Time to produce a finished flowering plant.*—About 12 months starting from a single 4-leaf rooted cutting with the plants pinched once in 15 cm to 20 cm pots.

*Root description.*—Thick, fleshy, white roots with finer lateral branches.

*Number of divisions or clumps per year.*—About four 4-leaf cuttings per year.

*Durability of foliage to stresses.*—Foliage holds up well against damage from shipping and handling; plants are durable and have excellent indoor keeping quality.

*High temperature tolerance.*—About 104° F. for several hours without damage.

*Low temperature tolerance.*—About 55° F. for several hours without damage.

Stems:

*Number of branches per plant.*—About 9.

*Type of branching.*—Basal.

*Length* (*from soil line to junction of the newest two leaves*).—5 cm to 7 cm.

*Diameter* (*measured from the midpoint*).—1.1 cm.

Internode length.—0.8 cm to 1.0 cm.

*Color.*—Immature: RHS 146B to RHS 146C and tinged with RHS 144A and RHS 164B. Mature: RHS 147A and RHS 146A and tinged with RHS 164B. Oldest stems: Between RHS 147A and RHS N189A.

*Shape and appearance.*—Columnar, cylindrical and upright.

*Aspect.*—Vertical and upright or leaning outward about 30 degrees; the apex of the stem is often turned up.

*Strength.*—Sturdy and somewhat flexible.

*Axillary buds.*—Shape: Elliptic, convex. Length: 0.6 cm. Width: 0.3 cm. Color: Between RHS 145C and RHS 146C.

Leaves:

*Arrangement.*—Alternate and simple; the leaves are arranged opposite along the stem; the leaf blade is mostly flat.

*Quantity of leaves per stem.*—2 to 3.

*Immature leaf* (*newly expanded leaf*).—Color: Upper surface: Base color is darker and greener than but closest to RHS 147A and variably marked with RHS 51B to RHS 51C to RHS 51D spots and coalescing blotches. Lower surface: Base color is RHS 147A and has an overall cast of RHS N186C; the upper surface patterns and markings are visible through to the lower surface of the leaf; the leaf blade is variably marked with RHS 52B to RHS 52C spots and coalescing blotches.

*Mature leaf.*—Color: Upper surface: Base color is darker and greener than but closest to RHS 147A and variably marked with RHS 146D spots and coalescing blotches tinged with RHS 49C and RHS 54A to RHS 54B. Lower surface: Base color is RHS 147A and has an overall cast of RHS N186C; the upper surface patterns and markings are visible through to the lower surface of the leaf; the leaf blade is variably marked with RHS 52B to RHS 52C spots and coalescing blotches.

*Length.*—17 cm to 21.5 cm.

*Width.*—Flattened: 11 cm to 15 cm. Not flattened: 10.5 cm to 14.5 cm.

*Shape.*—Ovate.

*Apex.*—Acuminate.

*Base.*—Obtuse.

*Margin.*—Smooth, entire and with some broad undulations.

*Texture.*—Upper surface: Smooth, supple and leathery; new leaves are shiny and mature leaves are glossy to dull; Lower Surface: Smooth and glossy; the leaf blade is convex between the main veins resulting in a textured appearance.

*Pubescence.*—Absent.

*Venation pattern.*—Pinnate and radiating outward from the midrib in a herringbone arrangement.

*Venation color.*—Immature leaf (newly expanded leaf): Upper surface: Primary veins: RHS 146D and tinged with RHS 49C. Midrib: Between RHS 148D and RHS 156D and tinged with RHS 49D at the proximal end and RHS 52B at the distal end. Lower surface: Primary veins: RHS 52C. Midrib: RHS 148A to RHS 148B at the proximal end and 52C at the distal end. Mature leaf: Upper surface: Primary veins: RHS 146D. Midrib: RHS 148D and streaked with RHS 148A at the proximal end and RHS 52B at the distal end. Lower surface: Primary veins: RHS 49C to RHS 49D. Midrib: RHS 148A to RHS 148B at the proximal end and RHS 52C to RHS 52D at the distal end.

Petioles:

*Aspect.*—Vertical and upright when newly expanded and becoming curved outward to about 45 degrees with maturity.

*Length.*—5.0 cm to 6.1 cm.

*Diameter.*—Distal: 0.4 cm. Proximal (petiole and petiole sheath clasps the stem proximally): Flattened: 2.4 cm. Not flattened: 1.1 cm. Depth (not flattened): 0.65 cm.

*Color.*—Distal (between the top of the wing and the base of the leaf): RHS 147A. with RHS 145D spots and often tinged overall with RHS 49D. Proximal: RHS 147A to RHS 147B with RHS 145D spots and streaks and often tinged overall with RHS 49D. Areas adjacent to the stem: RHS 146D and streaked with RHS 145D.

*Wing.*—Length: 1.5 cm to 2.0 cm. Diameter: Midpoint: 0.8 cm. Base: 1.1 cm. Depth: 0.65 cm. Color: Inside: RHS 157A tinged with RHS 185D. Outside: RHS 147A to RHS 147B with RHS 145D spots and streaks and often tinged with RHS 49D; margin is often flushed with RHS 185A and tinged with RHS 185C. Area adjacent to the stem: RHS 146D and streaked with RHS 145D.

*Cataphylls.*—Length: 3.3 cm to 7.0 cm. Width: 1.7 cm to 2.0 cm. Shape: Lanceolate, keeled and translucent. Apex: Cuspidate to emarginate. Base: Clasps the stem. Texture (inside and outside surfaces): Smooth and glossy. Color: Inside: RHS 49C tinged with RHS 48C. Outside: the proximal end is RHS 146D and RHS 145C and the distal end is RHS 48C to RHS 48D and often mottled with RHS 146B and RHS 146D.

Inflorescence:

*Appearance.*—Hooded spathes surrounding a columnar spadix are borne atop an upright peduncle; monoecious; the spadix is a central column of sessile, simple male and female flowers separated into two zones; the male flowers occupy the upper two-thirds of the spadix while the female flowers occupy the lower one-third of the spadix.

*Quantity of inflorescences per stem.*—About 2 to 3.
*Quantity of inflorescences per plant.*—About 8.
*Aspect.*—Upright.
*Height* (*from base of peduncle to tip of spathe*).—13.5 cm.
*Diameter/width.*—6.0 cm.
*Flowering habit.*—Seasonal; the natural flowering season is summer and fall as observed in Apopka, Fla. the flowers are persistent.
*Fragrance.*—Absent.
*Ratio of inflorescence to opening.*—About 1 new flower every 14 to 21 days.
*Peduncle.*—Length: 8.0 cm. Diameter: 0.5 cm. Aspect: Upright and often curved. Strength: Sturdy and flexible. Color: RHS 146A to RHS 146B.

Spathe:
*Appearance.*—Simple, hooded, cupped and enclosing the spadix.
*Aspect.*—Upright.
*Shape.*—Elliptic.
*Apex.*—Cuspidate.
*Base.*—Obtuse.
*Margin.*—Entire.
*Texture.*—Smooth and shiny on the inside and smooth and glossy on the outside.
*Size.*—Length: 5.9 cm. Width: 1.8 cm (not flattened) and 5.9 cm (flattened).
*Color* (*when opening*).—Front side: RHS 147C. Rear side: Greener than but closest to RHS 137B.
*Color* (*fully opened*).—Front side: RHS 147D. Rear side: RHS 146C to RHS 146D.
*Fading to.*—RHS 200A to RHS 200B.

Spadix:
*Appearance and shape.*—Columnar.
*Aspect.*—Upright.
*Size.*—Length: 4.3 cm. Diameter of the female zone: 1.1 cm. Diameter of the male zone: 1.1 cm. Length of the female zone: 0.9 cm. Length of the male zone: 3.4 cm.
*Apex.*—Obtuse.
*Base.*—Obtuse.
*Margin.*—Pebbled.
*Color.*—Female zone (immature): RHS 18B. Male zone (immature): RHS 9D. Female zone (mature): RHS 18A. Male zone (mature): RHS 8D.

Flowers:
*Type.*—Simple.
*Quantity of female flowers per spadix.*—280.
*Quantity of male flowers per spadix.*—280.
*Shape of female.*—Ovate to elliptic.
*Shape of male.*—Obovate, inverted triangle.
*Size.*—Female width: 0.25 cm. Male width: 0.19 cm. Female height and depth: 0.4 cm. Male height and depth: 0.3 cm.

Reproductive organs:
*Stigma color.*—RHS 18A.
*Ovary color.*—RHS 145D.
*Anther color.*—RHS 8D.

Fruit and seed set: None observed.

Disease and insect resistance: Typical of *Aglaonema* species; no particular susceptibility or resistance to pests or diseases noted.

COMPARISON WITH KNOWN VARIETIES

'TWYAG0022' differs from the commercial variety 'TWYAG0003' (U.S. Plant Pat. No. 17,673) in that 'TWYAG0022' is shorter (has a plant height of 15 cm to 21 cm), while 'TWYAG0003' is taller (has a plant height of about 27 cm). The leaf apex of 'TWYAG0022' is acuminate, while the leaf apex of 'TWYAG0003' is acute. Additionally, the leaf shape of 'TWYAG0022' is ovate, while the leaf shape of 'TWYAG003' is elliptic.

I claim:

1. A new and distinct cultivar of *Aglaonema* plant as shown and described herein.

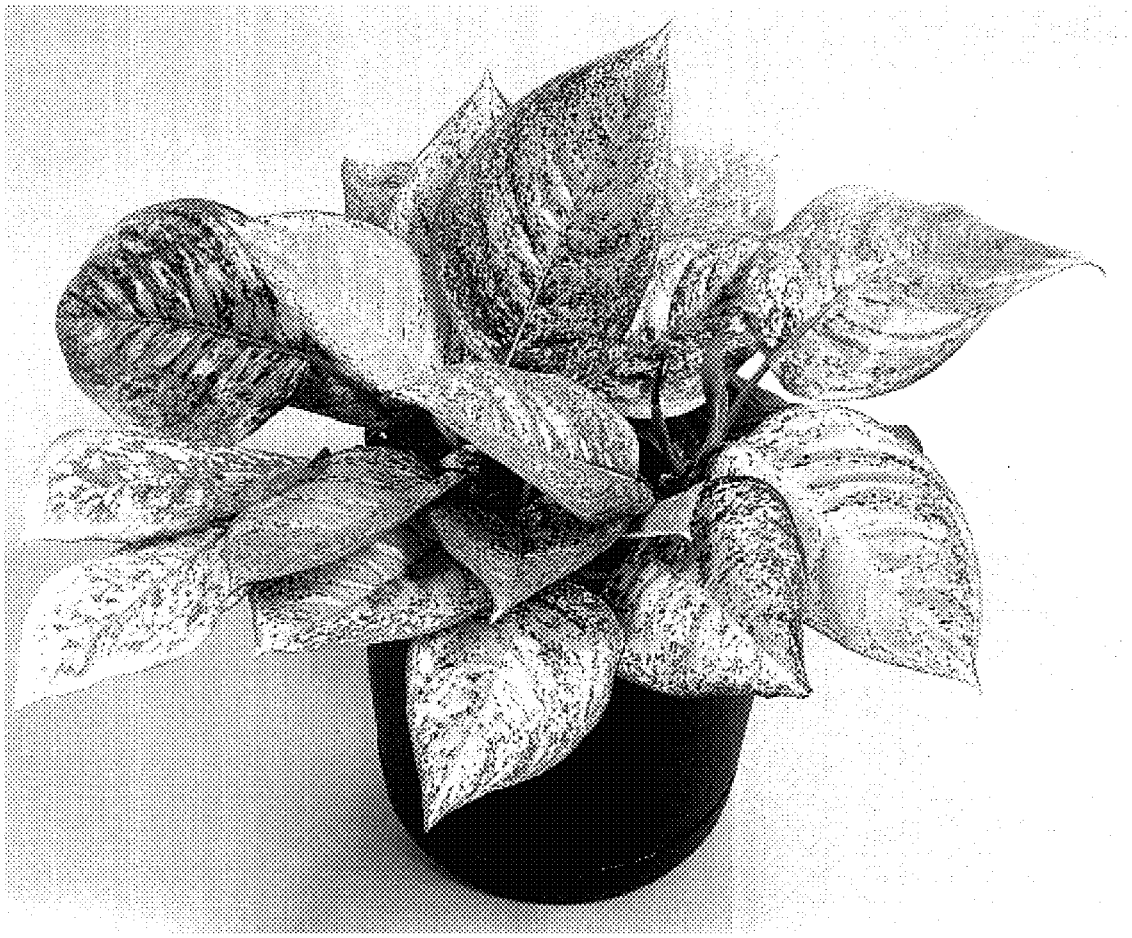

* * * * *